United States Patent
Ohashi et al.

(10) Patent No.: US 12,048,699 B2
(45) Date of Patent: Jul. 30, 2024

(54) CANCER TREATMENT METHODS BASED ON TP53 MUTATION STATUS AND HYPERMUTATION

(71) Applicant: TAKEDA PHARMACEUTICAL COMPANY LIMITED, Osaka (JP)

(72) Inventors: Akihiro Ohashi, Kanagawa (JP); Kenichi Iwai, Kanagawa (JP); Tadahiro Nambu, Kanagawa (JP); Kazunori Yamanaka, Kanagawa (JP); Kentaro Otake, Kanagawa (JP); Huifeng Niu, Cambridge, MA (US); Hyunjin Shin, Cambridge, MA (US); Erik Michael Koenig, Cambridge, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 775 days.

(21) Appl. No.: 17/252,400

(22) PCT Filed: Jun. 18, 2019

(86) PCT No.: PCT/JP2019/025995
§ 371 (c)(1),
(2) Date: Dec. 15, 2020

(87) PCT Pub. No.: WO2019/245061
PCT Pub. Date: Dec. 26, 2019

(65) Prior Publication Data
US 2021/0267980 A1 Sep. 2, 2021

Related U.S. Application Data

(60) Provisional application No. 62/686,960, filed on Jun. 19, 2018.

(51) Int. Cl.
*A61K 31/519* (2006.01)
*A61P 35/00* (2006.01)
*C12Q 1/6886* (2018.01)

(52) U.S. Cl.
CPC ............ *A61K 31/519* (2013.01); *A61P 35/00* (2018.01); *C12Q 1/6886* (2013.01); *C12Q 2600/106* (2013.01)

(58) Field of Classification Search
CPC .................................................. A61K 31/519
See application file for complete search history.

(56) References Cited

U.S. PATENT DOCUMENTS

2015/0320779 A1 11/2015 Fillmore et al.
2016/0024587 A1 1/2016 Che et al.

FOREIGN PATENT DOCUMENTS

| CN | 101283106 A | 10/2008 |
| CN | 105764516 A | 7/2016 |
| CN | 110325212 A | 10/2019 |
| WO | 2010006111 A2 | 1/2010 |
| WO | 2017172565 A1 | 10/2017 |
| WO | WO 2017/172565 A1 * | 10/2017 |

OTHER PUBLICATIONS

Hind Rafei et al., "Immune-based Therapies for Non-small Cell Lung Cancer", Anticancer Research—International Journal of Cancer Research and Treatment, vol. 37, No. 2, Feb. 10, 2017 (Feb. 10, 2017), p. 377-388.
Nambu, T. et al., "Identification of driver of anti-tumor activity of TAK-931 in human colorectal cancer xenograft model", European Journal of Cancer, vol. 69, Dec. 9, 2016 (Dec. 9, 2016).
Iwai, K. et al., "A novel CDC7-selective inhibitor TAK-931 with potent antitumor activity", European Journal of Cancer, vol. 69, Dec. 9, 2016 (Dec. 9, 2016).
Cortes-Ciriano, I. et al., "A molecular portrait of microsatellite instability across multiple cancers", Nature Communications, vol. 8, Jun. 6, 2017 (Jun. 6, 2017), p. 15180.
Olivier, M. et al., "TP53 Mutations in Human Cancers: Origins, Consequences, and Clinical Use", Cold Spring Harbor Perspectives in Biology, vol. 2, No. 1, Nov. 11, 2009 (Nov. 11, 2009), p. a001008-a001008.

* cited by examiner

*Primary Examiner* — Shawquia Jackson
(74) *Attorney, Agent, or Firm* — Honigman LLP; Lucy X. Yang; Jonathan P. O'Brien

(57) ABSTRACT

The present disclosure relates to methods useful for determining whether to treat cancer in a patient, and treating cancer in a patient, by administering a therapeutically effective amount of Compound 1 and/or tautomers thereof or a pharmaceutically acceptable salt or hydrate thereof.

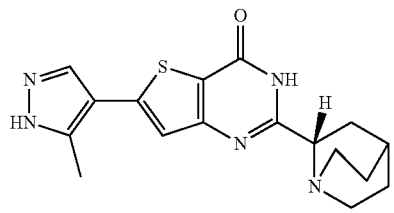

10 Claims, 2 Drawing Sheets

CANCER TREATMENT METHODS BASED ON TP53 MUTATION STATUS AND HYPERMUTATION

CROSS-REFERENCE TO RELATED APPLICATIONS

This application is a 35 U.S.C. § 371 United States National Phase Application of, and claims priority to, PCT Application No. PCT/JP2019/025995, filed Jun. 18, 2019, which claims the priority benefit of U.S. Provisional Patent Application No. 62/686,960, filed Jun. 19, 2018. The entire contents of the aforesaid applications are incorporated by reference herein in its entirety.

TECHNICAL FIELD

The present disclosure relates to methods useful for determining whether to treat cancer in a patient, and treating cancer in a patient, by administering a therapeutically effective amount of Compound 1 and/or tautomers thereof or a pharmaceutically acceptable salt or hydrate thereof.

Compound 1

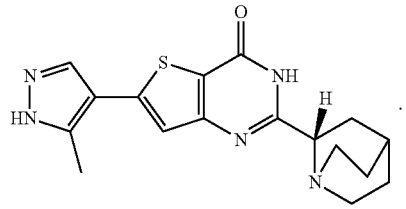 [SMILES: Cc1[nH]ncc1-c1cc2nc([C@@H]3CC4CCN3CC4)[nH]c(=O)c2s1]

Background

Cdc7 is an evolutionarily well-conserved serine/threonine kinase and plays an important role in the initiation of DNA replication (EMBO J. 1999, 18(20), p. 5703-5713). The kinase activity of Cdc7 is controlled by binding with its activating partner thereof. From the late stage of G1 phase to S phase, Cdc7 forms a complex with Dbf4 (also known as ASK) and phosphorylates Cdc7 substrate to control transition from the G1 phase to the S phase (J Cell Physiol. 2002, 190(3), p. 287-296). Furthermore, recent studies have reported that Cdc7 plays important roles in both DNA replication and DNA damage signaling pathways (Oncogene. 2008, 27(24), p. 3475-3482).

Cdc7 kinase has received attention as an attractive target in cancer treatments. Overexpression of Cdc7 is observed in clinical tumors such as breast cancer, colorectal cancer, lung cancer and the like, and many cancer cell lines (Neoplasia. 2008, 10(9), p. 920-931). In some cancer cell lines, an increase in chromosomal copy number of an activating factor, Dbf4, is found. Interestingly, a cancer cell line and an untransformed fibroblast cell line show different responses to suppression of Cdc7 expression using siRNA. The suppression of Cdc7 expression using siRNA causes the S phase arrest in cancer cell lines and induces apoptosis, whereas in normal cells it induces the G1 phase arrest in a p53 activity-dependent manner (Cancer Res. 2004, 64(19), p. 7110-7116). Furthermore, Cdc7 kinase is activated in the cells under replication stress, and apoptosis induced by hydroxyurea and etoposide increases in the Cdc7 down-regulated cells (J Biol Chem. 2007, 282(1), p. 208-215).

Thus, a Cdc7 inhibitor, as a single agent or in combination with other chemotherapeutic agents, is useful for a selective cancer treatment.

SUMMARY

In one aspect, the present disclosure provides a method of determining whether to treat a patient with cancer with Compound 1 and/or tautomers thereof or a pharmaceutically acceptable salt or hydrate thereof, wherein Compound 1 has the structure:

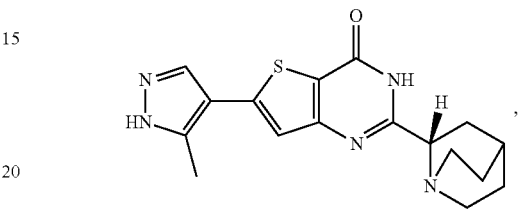

comprising: determining a TP53 mutation status and/or a hypermutation status (e.g., both) from one or more samples from the patient, and determining to treat the patient with a therapeutically effective amount of Compound 1 and/or tautomers thereof or a pharmaceutically acceptable salt or hydrate thereof if the one or more samples (i) have the presence of TP53 mutation(s) and/or (ii) test negative for hypermutation (e.g., both (i) and (ii)). In some embodiments, the method further comprises administering a therapeutically effective amount of Compound 1 and/or tautomers thereof or a pharmaceutically acceptable salt or hydrate thereof to the patient if the one or more samples (i) have the presence of TP53 mutation(s) and/or (ii) test negative for hypermutation (e.g., both (i) and (ii)).

Another aspect of the present disclosure provides a method of treating cancer comprising: determining a TP53 mutation status and/or a hypermutation status (e.g., both) of one or more samples from a patient, and administering a therapeutically effective amount of Compound 1 and/or tautomers thereof or a pharmaceutically acceptable salt or hydrate thereof to the patient if the one or more samples (i) have the presence of TP53 mutation(s) and/or (ii) test negative for hypermutation (e.g., both (i) and (ii)).

Another aspect of the present disclosure provides a method of treating cancer comprising administering a therapeutically effective amount of Compound 1 and/or tautomers thereof or a pharmaceutically acceptable salt or hydrate thereof to a patient in need thereof.

Another aspect of the present disclosure provides a pharmaceutical composition comprising Compound 1 and/or tautomers thereof or a pharmaceutically acceptable salt or hydrate thereof for use in treating cancer.

Numerous embodiments of the aspects of the invention are described herein.

In some embodiments, a sample tests negative for hypermutation if the sample has microsatellite stability (MSS) status.

In some embodiments, the cancer is a cancer associated with TP53 mutation(s) and/or hypermutation status.

In some embodiments, the cancer (i) has the presence of TP53 mutation(s) and (ii) tests negative for hypermutation.

In some embodiments, the cancer is selected from squamous esophageal cancer and squamous non-small cell lung cancer.

In some embodiments, the cancer is squamous esophageal cancer.

In some embodiments, the cancer is squamous non-small cell lung cancer.

In some embodiments, the cancer is locally advanced or metastatic squamous esophageal cancer or locally advanced or metastatic squamous non-small cell lung cancer.

In some embodiments, the Compound 1 and/or tautomers thereof or a pharmaceutically acceptable salt or hydrate thereof is a hemihydrate of Compound 1.

In some embodiments, the hemihydrate of Compound 1 is Crystalline Form I of the hemihydrate of Compound 1.

DETAILED DESCRIPTION

Figure 1:
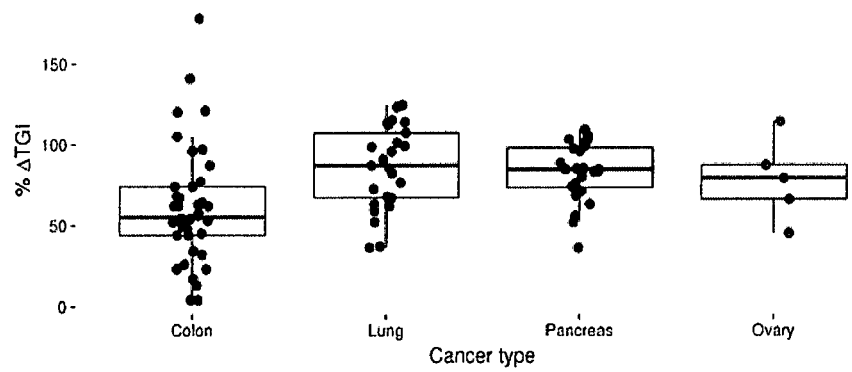
FIG. 1 is a plot of % ΔTGI by cancer type of the phase 2 like data.

The present disclosure relates to use of predictive biomarkers for predicting resistance or sensitivity to therapy with Compound 1 and/or tautomers thereof or a pharmaceutically acceptable salt or hydrate thereof prior to or concurrent with treatment, in addition to methods of treating patients with such resistance or such sensitivity and the treatment regimens related thereto. The present disclosure also relates to methods of treating cancer comprising administering a therapeutically effective amount of Compound 1 and/or tautomers thereof or a pharmaceutically acceptable salt or hydrate thereof to a patient in need thereof.

In certain embodiments, the disclosure relates to predictive biomarkers relative to therapy with the Cdc7 kinase inhibitor, 2-[(2S)-1-azabicyclo[2.2.2]oct-2-yl]-6-(3-methyl-1H-pyrazol-4-yl)thieno[3,2-d]pyrimidin-4(3H)-one (Compound 1)

Compound 1

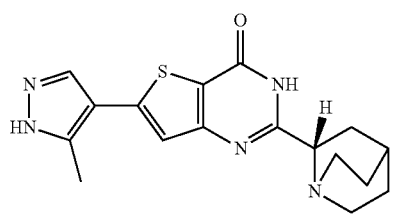

and/or tautomers thereof or a pharmaceutically acceptable salt or hydrate thereof.

In certain embodiments, cancers with TP53 mutation(s) may be more sensitive to Compound 1 and/or tautomers thereof or a pharmaceutically acceptable salt or hydrate thereof as compared to cancers without TP53 mutation (i.e., TP53 mutation status is a predictive biomarker for cancer treatment with Compound 1 and/or tautomers thereof or a pharmaceutically acceptable salt or hydrate thereof). In certain embodiments, cancers with non-hypermutated status (e.g., with microsatellite stability (MSS) status) may be more sensitive to Compound 1 and/or tautomers thereof or a pharmaceutically acceptable salt or hydrate thereof as compared to cancers with hypermutated status (e.g., with low microsatellite instability status (MSI-L) status or with high microsatellite instability (MSI-H) status) (i.e., non-hypermutated status (e.g., MSS status) is a predictive biomarker for cancer treatment with Compound 1 and/or tautomers thereof or a pharmaceutically acceptable salt or hydrate thereof). In certain embodiments, cancers with non-mutated status of CHD family genes may be more sensitive to Compound 1 and/or tautomers thereof or a pharmaceutically acceptable salt or hydrate thereof as compared to cancers with mutated status of CHD family genes (i.e., non-mutated status of CHD family genes is a predictive biomarker for cancer treatment with Compound 1 and/or tautomers thereof or a pharmaceutically acceptable salt or hydrate thereof). In certain embodiments, ovarian serous cystadenocarcinoma, esophageal carcinoma (e.g., squamous esophageal cancer), lung squamous cell carcinoma (e.g., squamous non-small cell lung cancer), head and neck squamous cell carcinoma, rectum/colon adenocarcinoma and pancreatic adenocarcinoma etc. may be treated by administration of Compound 1 and/or tautomers thereof or a pharmaceutically acceptable salt or hydrate thereof and optionally in conjunction with use of the predictive biomarker(s). Further, in certain embodiments, non-small cell lung cancer, and in particular, squamous non-small cell lung cancer may be treated by administration of Compound 1 and/or tautomers thereof or a pharmaceutically acceptable salt or hydrate thereof and optionally in conjunction with use of the predictive biomarker(s). In certain embodiments, esophageal cancer, and in particular, squamous esophageal cancer may be treated by administration of Compound 1 and/or tautomers thereof or a pharmaceutically acceptable salt or hydrate thereof and optionally in conjunction with use of the predictive biomarker(s).

The TP53 gene provides instructions for making a protein called tumor protein p53 (or p53). This protein acts as a tumor suppressor, which means that it regulates cell division by keeping cells from growing and dividing (proliferating) too fast or in an uncontrolled way. Somatic mutations in the TP53 gene are one of the most frequent alterations in human cancers. See Olivier et al. TP53 Mutations in Human Cancers: Origins, Consequences, and Clinical Use. *Cold Spring Harbor Perspectives in Biology.* 2010; 2(1):a001008. doi: 10.1101/cshperspect.a001008. A tumor sample may be determined to have the presence of TP53 mutation(s) according to any generally accepted methods and criteria.

A hypermutated tumor is defined as a tumor with an increased mutation burden (a high rate of somatic mutation). The threshold above which tumors are considered hypermutated depends on the sequencing methodology and type of cancer. See Yuza et al. Hypermutation and microsatellite instability in gastrointestinal cancers. *Oncotarget.* 2017; 8(67):112103-112115. doi:10.18632/oncotarget.22783. A tumor sample may be determined as testing positive or negative for hypermutation according to any generally accepted methods and criteria. One method of testing for hypermutation is to test for microsatellite instability (MSI), which is a well-established tumorigenesis pathway that refers to the hypermutable state of cells, and can be used as a measure of hypermutation.

Microsatellite instability (MSI) refers to the hypermutability of short repetitive sequences in the genome caused by impaired DNA mismatch repair. Microsatellites (MS) are tandem repeats of short DNA sequences, abundant throughout the human genome. Owing to their high mutation rates, MS have been used as polymorphic markers in population genetics and forensics. See Cortes-Ciriano et al. A molecular portrait of microsatellite instability across multiple cancers. *Nature Communications.* 2017; 8:15180. doi:10.1038/ncomms15180. One non-limiting example of a generally accepted criteria for MSI status is the Bethesda Guidelines, which were established in 1997 and revised in 2004. According to some criteria, microsatellite instability/stability (MSI/MSS) status can be classified into three groups: MSI-high (MSI-H), MSI-low (MSI-L) and MSS. Thus, in some embodiments of this disclosure, determination of hypermutation status (e.g., MSI/MSS status) comprises classifying the sample as MSI-H, MSI-L or MSS according to any generally accepted methods and criteria. In some embodiments, MSS is used as a predictive biomarker for cancer treatment with Compound 1 and/or tautomers thereof or a pharmaceutically acceptable salt or hydrate thereof.

CHD gene means chromodomain helicase DNA-binding proteins, and CHD family gene include CHD1, CHD1L, CHD2, CHD3, CHD4, CHD5, CHD6, CHD7 and CHD8 etc. 'Non-mutated status of CHD family genes' means that any mutation is not found in CHD family gene.

Accordingly, aspects of the present disclosure relate to the use of one or both of TP53 mutation status and hypermutation status for determining whether to treat a patient with cancer. Another aspects of the present disclosure relate to the combinational use of TP53 mutation status, hypermutation status and CHD family gene mutation status for determining whether to treat a patient with cancer. In certain embodiments, the cancer is ovarian serous cystadenocarcinoma, esophageal carcinoma (e.g., squamous esophageal cancer), lung squamous cell carcinoma (e.g., squamous non-small cell lung cancer), head and neck squamous cell carcinoma, rectum/colon adenocarcinoma or pancreatic adenocarcinoma. In some embodiments the cancer is NSCLC (e.g., squamous NSCLC). In some embodiments, the cancer is esophageal cancer (e.g., squamous esophageal cancer). In some embodiments, TP53 is used as the predictive biomarker without use of hypermutation status, but optionally with one or more additional biomarker(s). In some embodiments, TP53 is used as the sole predictive biomarker. In some embodiments, hypermutation status is used as the predictive biomarker without use of TP53 status, but optionally with one or more additional biomarkers. In some embodiments, CHD family genes mutation status is used as the predictive biomarker without use of TP53 status or hypermutation status, but optionally with one or more additional biomarkers. In some embodiments, hypermutation status is used as the sole predictive biomarker. In some embodiments, TP53 and hypermutation status are used in combination as predictive biomarkers, optionally with one or more additional biomarkers. In some embodiments, the additional biomarker is CHD family gene. In some embodiments, the combination of TP53 and hypermutation status are used as the exclusive predictive biomarkers, without additional biomarkers.

In one aspect, the present disclosure provides a method of predicting the likelihood that a patient will respond therapeutically to a cancer treatment comprising the administration of Compound 1 and/or tautomers thereof or a pharmaceutically acceptable salt or hydrate thereof, which comprises determining a TP53 mutation status, hypermutation status, or both, of a sample from a patient. In some embodiments the cancer is NSCLC (e.g., squamous NSCLC). In some embodiments, the cancer is esophageal cancer (e.g., squamous esophageal cancer).

In one embodiment, the method of the present disclosure comprises (1) determining a TP53 mutation status, hypermutation status, or both, of a sample from a patient with one or more additional biomarkers (e.g., CHD family gene), and (2) predicting an increased likelihood that the patient will respond therapeutically to the cancer treatment based on the status(es)—specifically, predicting an increased likelihood that the patient will respond therapeutically to the cancer treatment if the sample(s) tests positive for TP53 mutation (or negative for wild-type TP53), tests negative for MSI (or positive for MSS), or both.

In some embodiments, the method of the present disclosure comprises a step such as following STEP (1) to determine the mutation status of a sample taken from a cancer patient. In some embodiments, the STEP (1) to determine the mutation status of a sample taken from a cancer patient is not required. In some embodiments, STEP (1) is not required, e.g., when it is inferred that the cancer (i) has the presence of TP53 mutation(s) and/or (ii) is non-hypermutated (e.g., both (i) and (ii)) based on, for example, information of cancer species.

Examples of the sample used in STEP (1) may be a biological sample which includes, but are not limited to, serum, whole fresh blood, peripheral blood mononuclear cells, frozen whole blood, fresh plasma, frozen plasma, urine, saliva, skin, hair follicle, bone marrow, tumor tissue, tumor biopsy, or archived paraffin-embedded tumor tissue. The sample is preferably tumor tissue or tumor biopsy comprising cancer cells.

The status of the gene mutation may be, for example, at the level of genomic DNA, protein and/or mRNA transcript of the gene. Preferably, presence or absence of mutation in the gene is determined at the level of genomic DNA or mRNA transcript.

Methods for determining the TP53 mutation status, hypermutation (e.g., MSI/MSS) status and CHD family gene mutation status are well known in the art. Examples of such method include, but are not limited to, RFLP (Restriction Fragment Length Polymorphism) method, PCR-SSCP (Single Strand DNA Conformation Polymorphism) method, ASO (Allele Specific Oligonucleotide) hybridization method, sequencing method, ARMS (Amplification Refracting Mutation System) method, denaturing gradient gel electrophoresis method, RNAse A cleavage method, DOL (Dye-labeled Oligonucleotide Ligation) method, TaqMan PCR method, primer extension method, invader method, Scorpion-ARMS method, F-PHFA method, pyrosequence method, BEAMing method, RT-PCR, FISH, IHC, immunodetection method, Western Blot, ELISA, radioimmune assay, immunoprecipitation, FACS, HPLC, surface plasmon resonance, optical spectroscopy, and mass spectrometry. In particular, next generation sequencing methods, e.g., whole exome sequencing (WES) and RNA sequencing (RNASeq) may be used.

As shown in the Examples, cancers with TP53 mutation(s) and/or non-hypermutated status (e.g., MSS status) may be expected to be more sensitive to Compound 1 and/or tautomers thereof or a pharmaceutically acceptable salt or hydrate thereof as compared to cancers without TP53 mutation(s) and with hypermutated status (e.g., MSI-L or MSI-H status). Based on these results, if the sample is positive for TP53 mutation(s) and/or negative for hypermutation (especially, if the sample is positive for TP53 mutation(s) and negative for hypermutation), then an increased likelihood that the cancer will respond to treatment with Compound 1 and/or tautomers thereof or a pharmaceutically acceptable salt or hydrate thereof may be predicted. Accordingly, it may be determined to treat the cancer in the patient with Compound 1 and/or tautomers thereof or a pharmaceutically acceptable salt or hydrate thereof. If the mutation status is negative for TP53 mutation(s) and/or positive for hypermutation (e.g., MSI-L or MSI-H status) (especially, if the sample is negative for TP53 mutation(s) and positive for hypermutation), then the likelihood that the patient and the cancer in the patient will not respond therapeutically to the treatment with Compound 1 and/or tautomers thereof or a pharmaceutically acceptable salt or hydrate thereof may be predicted.

The Examples also show that cancers with both TP53 mutation(s) and non-hypermutated status (e.g., MSS status) may be expected to be sensitive to Compound 1 and/or tautomers thereof or a pharmaceutically acceptable salt or hydrate thereof. Based on these results, if the sample is positive for TP53 mutation(s) and negative for hypermutation, then an increased likelihood that the cancer will respond to treatment with Compound 1 and/or tautomers thereof or a pharmaceutically acceptable salt or hydrate thereof may be predicted. Further, the Examples also show non-mutation status of CHD family gene may be expected to be sensitive to Compound 1 and/or tautomers thereof or a pharmaceutically acceptable salt or hydrate thereof. Accordingly, it may be determined to treat the cancer in the patient with Compound 1 and/or tautomers thereof or a pharmaceutically acceptable salt or hydrate thereof.

In some embodiments, the cancer in the patient is regarded as hypermutated if the sample from the patient has mutations in more than 2 genes among the genes which tested for hypermutation. As shown in the Examples, as the genes which tested for hypermutation, the following genes are exemplified: TP53, ACVR2A, LRP1B, CTNNB1, SEC31A, ABCB4, HERC2, DNM2, FXR1, BAX, ATR, APC, CHD8, CTCF, CHD2, PIK3CA, CLOCK, CNOT1, STAT5B and CHD3.

A patient with a cancer may be treated by administering a therapeutically effective amount of Compound 1 and/or tautomers thereof or a pharmaceutically acceptable salt or hydrate thereof if said patient is predicted, according to the above-mentioned method of the present disclosure, to have an increased likelihood of therapeutic response to a cancer treatment comprising the administration of Compound 1 and/or tautomers thereof or a pharmaceutically acceptable salt or hydrate thereof. In some embodiments the cancer is NSCLC (e.g., squamous NSCLC). In some embodiments, the cancer is esophageal cancer (e.g., squamous esophageal cancer).

In the aforementioned method described herein, if a patient is not predicted to have an improved likelihood of therapeutic response to Compound 1 and/or tautomers thereof or a pharmaceutically acceptable salt or hydrate thereof by the administration of Compound 1 and/or tautomers thereof or a pharmaceutically acceptable salt or hydrate thereof, said patient may be discontinued treatment with Compound 1 and/or tautomers thereof or a pharmaceutically acceptable salt or hydrate thereof.

In one aspect, the present disclosure relates to methods of treating cancer comprising administering a therapeutically effective amount of Compound 1 and/or tautomers thereof or a pharmaceutically acceptable salt or hydrate thereof to a patient in need thereof. In some embodiments, the cancer is a cancer mediated by Cdc7 (for example, colorectal cancer (e.g., metastatic colorectal cancer), lung cancer (e.g., non-small cell lung cancer (e.g., squamous non-small cell lung cancer (including locally advanced squamous non-small cell lung cancer and metastatic squamous non-small cell lung cancer)), mesothelioma, pancreatic cancer (e.g., metastatic pancreatic cancer), pharyngeal cancer, laryngeal cancer, esophageal cancer (e.g., squamous esophageal cancer), gastric cancer duodenal cancer, small intestinal cancer, breast cancer, ovarian cancer, testis tumor, prostate cancer, liver cancer, thyroid cancer, kidney cancer, uterine cancer, brain tumor, retinoblastoma, skin cancer, bone tumor, urinary bladder cancer, hematologic cancer (e.g., multiple myeloma, leukemia, malignant lymphoma, Hodgkin's disease, chronic bone marrow proliferative disease). Particularly, Compound 1 and/or tautomers thereof or a pharmaceutically acceptable salt or hydrate thereof is effective for the cancer selected from a group consisting of pancreatic cancer (e.g., metastatic pancreatic cancer), colorectal cancer (e.g., metastatic colorectal cancer), esophageal cancer (e.g., squamous esophageal cancer (including locally advanced squamous esophageal cancer and metastatic squamous esophageal cancer)) and non-small cell lung cancer (e.g., squamous non-small cell lung cancer (for example, locally advanced squamous non-small cell lung cancer or metastatic squamous non-small cell lung cancer)). In certain embodiments, Compound 1 and/or tautomers thereof or a pharmaceutically acceptable salt or hydrate thereof may be effective for treating a cancer selected from squamous esophageal cancer (including locally advanced squamous esophageal cancer and metastatic squamous esophageal cancer) and squamous non-small cell lung cancer (including locally advanced squamous non-small cell lung cancer and metastatic squamous non-small cell lung cancer). In some embodiments, the cancer is a cancer that (i) has the presence of TP53 mutation(s) and (ii) tests negative for hypermutation.

In some embodiments, the cancer is ovarian serous cystadenocarcinoma, esophageal carcinoma (e.g., squamous esophageal cancer), lung squamous cell carcinoma (e.g., squamous non-small cell lung cancer), head and neck squamous cell carcinoma, rectum/colon adenocarcinoma or pancreatic adenocarcinoma. In some embodiments, the cancer is squamous esophageal cancer. In some embodiments, the cancer is squamous non-small cell lung cancer (squamous NSCLC). In some embodiments, the squamous esophageal cancer is locally advanced or metastatic. In some embodiments, the squamous NSCLC is locally advanced or metastatic.

In another aspect, the present disclosure relates to a pharmaceutical composition comprising Compound 1 and/or tautomers thereof or a pharmaceutically acceptable salt or hydrate thereof for use in treating cancer, wherein the cancer is selected from squamous esophageal cancer and squamous non-small cell lung cancer.

In another aspect, the present disclosure relates to use of a pharmaceutical composition comprising Compound 1 and/or tautomers thereof or a pharmaceutically acceptable salt or hydrate thereof for the manufacture of a medicament for treating cancer, wherein the cancer is selected from squamous esophageal cancer and squamous non-small cell lung cancer.

In another aspect, the present disclosure relates to a pharmaceutical composition comprising Compound 1 and/or tautomers thereof or a pharmaceutically acceptable salt or hydrate thereof for use in treating cancer, wherein the cancer (i) has the presence of TP53 mutation(s) and (ii) tests negative for hypermutation.

Definitions

Unless defined otherwise, all technical and scientific terms used herein have the same meaning as commonly understood by one of ordinary skill in the art to which this disclosure belongs. Accordingly, the following terms are intended to have the following meanings:

As used in the specification and claims, the singular form "a", "an" and "the" includes plural references unless the context clearly dictates otherwise.

As used herein, "administration" of a disclosed compound encompasses the delivery to a subject of a compound as described herein, or a prodrug or other pharmaceutically acceptable derivative thereof, using any suitable formulation or route of administration, e.g., as described herein.

As used herein, "effective amount" or "therapeutically effective amount" refers to the amount of a compound or pharmaceutical composition described herein that is sufficient to effect the intended application including, but not limited to, disease treatment, as illustrated below. In some embodiments, the amount is that effective for detectable killing or inhibition of the growth or spread of cancer cells; the size or number of tumors; or other measure of the level, stage, progression or severity of the cancer. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, "treatment" and "treating", are used interchangeably herein, and refer to an approach for obtaining beneficial or desired results including, but not limited to, therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

As used herein, "subject" or "patient" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys).

Compound 1

Compound 1 has the following structure:

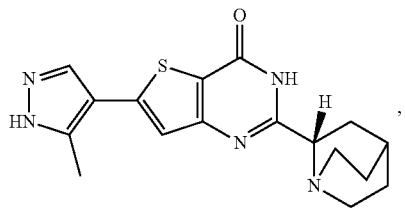 [SMILES: Cc1[nH]ncc1-c1cc2nc([C@@H]3CC4CCN3CC4)[nH]c(=O)c2s1]

The chemical name for Compound 1 is 2-[(2S)-1-azabicyclo[2.2.2]oct-2-yl]-6-(3-methyl-1H-pyrazol-4-yl)thieno[3,2-d]pyrimidin-4(3H)-one. Compound 1 is a Cdc7 kinase inhibitor.

Tautomers of Compound 1 or a pharmaceutically acceptable salt or hydrate of Compound 1 are/is also encompassed by the present disclosure. When Compound 1 has a tautomer, each isomer is also encompassed in the present disclosure.

As used herein the phrases "Compound 1 and/or tautomers thereof" and the like are all understood to mean Compound 1 and all of its tautomeric forms. As a non-limiting example, tautomerization may occur in the pyrazole and pyrimidine groups of Compound 1. Specific examples of tautomerization that may occur in Compound 1 include:

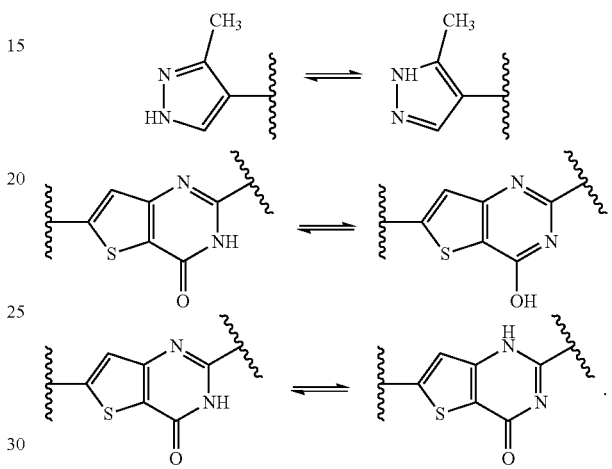

Compound 1 and/or tautomers thereof can be used in the form of a pharmaceutically acceptable salt. Examples of the pharmaceutically acceptable salt include salts with inorganic bases, salts with organic bases, salts with inorganic acids, salts with organic acids, and salts with basic or acidic amino acids.

Compound 1 and/or tautomers thereof may be a hydrate (e.g., hemihydrate), a non-hydrate, a solvate or a non-solvate, all of which are encompassed in the present disclosure. In some embodiments, Compound 1 and/or tautomers thereof is a hemihydrate.

Compound 1 and/or tautomers thereof or a pharmaceutically acceptable salt or hydrate thereof or a crystal form thereof can be obtained according to the production methods described in PCT Publication No. WO 2011/102399, U.S. Pat. Nos. 8,722,660, 8,921,354, 8,933,069, and U.S. Patent Publication No. US 2015/158882, which are incorporated herein by reference in their entirety and for all purposes, or a method analogous thereto.

Compound 1 and/or tautomers thereof or a pharmaceutically acceptable salt or hydrate thereof may be in the form of a crystal (e.g., crystalline form A, crystalline form I, etc.), and the crystal form of the crystal may be single or plural, both of which are encompassed in Compound 1. The crystal may be of a form, and can be produced by a method, described in PCT publication no. WO 2017/172565, published Oct. 5, 2017, which is incorporated herein by reference in its entirety for all purposes. In some embodiments, the Compound 1 and/or tautomers thereof or a pharmaceutically acceptable salt or hydrate thereof may be in the form of Crystalline Form I as described in WO 2017/172565. In some embodiments, the Compound 1 and/or tautomers thereof or a pharmaceutically acceptable salt or hydrate thereof is a crystalline form of Compound 1 hemihydrate (i.e., 2-[(2S)-1-azabicyclo[2.2.2]oct-2-yl]-6-(3-methyl-1H- pyrazol-4-yl)thieno[3,2-d]pyrimidin-4(3H)-one hemihydrate). For example, the Compound 1 and/or tautomers thereof or a pharmaceutically acceptable salt or hydrate thereof may be Crystalline Form I of Compound 1 hemihydrate.

Pharmaceutical Compositions

Compound 1 and/or tautomers thereof or a pharmaceutically acceptable salt or hydrate thereof may be administered, as a medicament, orally or parenterally, alone or in a mixture with a pharmaceutically acceptable carrier, to the aforementioned patient.

The medicament comprising Compound 1 and/or tautomers thereof or a pharmaceutically acceptable salt or hydrate thereof (sometimes to be abbreviated as "the medicament for use in the present disclosure") is explained in detail herein. The medicament for use in the present disclosure can be used in the methods of treating cancer as described herein.

The medicament comprising Compound 1 and/or tautomers thereof or a pharmaceutically acceptable salt or hydrate thereof can be administered orally or parenterally as it is or in a mixture with a pharmaceutically acceptable carrier (sometimes referred to as a pharmaceutically acceptable excipient).

Examples of the dosage form of the medicament of the present disclosure for oral administration of the compound of the present disclosure (i.e., Compound 1 and/or tautomers thereof or a pharmaceutically acceptable salt or hydrate thereof) include oral preparations such as tablet (including sugar-coated tablet, film-coated tablet, sublingual tablet, buccal tablet, fast disintegration oral tablet), pill, granule, powder, capsule (including soft capsule, microcapsule), syrup, emulsion, suspension and films (e.g., oral mucosal adhesive film). Examples of the dosage form of the medicament of the present disclosure for parenteral administration include injection, impregnate, drip infusion, transdermal agent (e.g., iontophoresis transdermal agent) and suppository. It is also effective to prepare a sustained-release preparation by combining the compound of the present disclosure with a suitable base (e.g., butyric acid polymer, glycolic acid polymer, butyric acid-glycolic acid copolymer, a mixture of butyric acid polymer and glycolic acid polymer, polyglycerol fatty acid ester).

The medicament of the present disclosure can be produced by a known production method generally used in the technical field of pharmaceutical preparations. In addition, the medicament of the present disclosure can appropriately contain, where necessary, appropriate amounts of pharmaceutically acceptable carrier generally used in the pharmaceutical field, such as excipient, binder, disintegrant, lubricant, sweetener, surfactant, suspending agent, emulsifier, colorant, preservative, aromatic, corrigent, stabilizer, thickener and the like. Examples of the aforementioned pharmacologically acceptable carrier include these additives.

For example, tablet can be produced by using excipient, binder, disintegrant, lubricant and the like, and pill and granule can be produced by using excipient, binder and disintegrant. In addition, powder and capsule can be produced by using excipient and the like, syrup can be produced by using sweetener and the like, and emulsion and suspension can be produced by using suspending agent, surfactant, emulsifier and the like.

Examples of the excipient include lactose, refined sugar, glucose, starch, sucrose, crystalline cellulose, powdered *Glycyrrhiza*, mannitol, sodium hydrogen carbonate, calcium phosphate and calcium sulfate.

Examples of the binder include 5-10 wt % starch liquid paste, 10-20 wt % gum arabic solution or gelatin solution, 1-5 wt % tragacanth solution, carboxymethyl cellulose solution, sodium alginate solution and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethyl cellulose, methyl cellulose and bentonite.

Examples of the emulsifier include gum arabic, tragacanth, gelatin, polysorbate 80.

For example, when the medicament of the present disclosure is in the form of a tablet, the tablet can be produced according to a method known per se, by adding, for example, excipient (e.g., lactose, refined sugar, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol 6000) to the compound of the present disclosure, compression molding the mixture, and then, where necessary, applying a coating by a method known per se for the purpose of masking taste, enteric coating or sustainability. Examples of the coating agent used for coating include hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) and dye (e.g., red iron oxide, titanium dioxide). The thus-obtained tablet may be any of immediate-release preparation and sustained-release preparation.

Examples of the aforementioned injection include intravenous injection as well as subcutaneous injection, intracutaneous injection, intramuscular injection, instillation and the like.

Such injections are prepared by methods known per se, or by dissolving, suspending or emulsifying the compound of the present disclosure in a sterilized aqueous or oily liquid. Examples of the aqueous liquid include isotonic solution containing saline, glucose and other auxiliary agents (e.g., D-SORBITOL, D-mannitol, sodium chloride) and the like. The aqueous liquid may contain suitable solubilizing agents, for example, alcohol (e.g., ethanol), polyalcohol (e.g., propylene glycol, polyethylene glycol), and non-ionic surfactant (e.g., polysorbate 80, HCO-50). Examples of the oil liquid include sesame oil, soybean oil and the like. The oil liquid may contain suitable solubilizing agents. Examples of the solubilizing agents include benzyl benzoate, benzyl alcohol and the like. In addition, the injection may contain buffering agents (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and the like. A prepared injection is generally filled in an ampoule.

While the content of the compound of the present disclosure in the medicament of the present disclosure varies depending on the form of the pharmaceutical preparation, it is generally about 0.01 to 100 wt %, preferably about 2 to 85 wt %, more preferably about 5 to 70 wt %, relative to the entire preparation.

While the content of the additive in the medicament of the present disclosure varies depending on the form of the pharmaceutical preparation, it is generally about 1 to 99.9 wt %, preferably about 10 to 90 wt %, relative to the entire preparation.

Dosage and Administration

Compound 1 and/or tautomers thereof or a pharmaceutically acceptable salt or hydrate thereof is stable and has low toxicity, and can be used safely. While the daily dose varies depending on the condition and body weight of the patient, administration route and the like, in the case of, for example, Compound 1 and/or tautomers thereof or a pharmaceutically acceptable salt or hydrate thereof may be administered orally in the form of a medicament described herein to a patient for treatment.

In some embodiments, the medicament for use in the present disclosure comprises a dose strength of Compound 1 and/or tautomers thereof or a pharmaceutically acceptable salt or hydrate thereof ranging from 10 to 200 mg. For example, in some embodiments, a medicament comprises a dose strength of 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg of Compound 1 and/or tautomers thereof or a pharmaceutically acceptable salt or hydrate thereof. In some embodiments, the daily dose administered to an adult (body weight about 60 kg) ranges from 10 to 200 mg. In other embodiments, the daily dose to an adult (body weight about 60 kg) is about 1 to 1000 mg, preferably about 3 to 300 mg, more preferably about 10 to 200 mg, as the compound of the present disclosure, which can be given in a single administration or administered in 2 or 3 portions a day.

The compound of the present disclosure (i.e., Compound 1 and/or tautomers thereof or a pharmaceutically acceptable salt or hydrate thereof) can be administered, as a medicament, orally or parenterally, alone or in a mixture with a pharmacologically acceptable carrier, to the patient. In some embodiments, the compound of the present disclosure is administered orally.

When the compound of the present disclosure is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, relative to 1 kg body weight, which is preferably intravenous injection.

In some embodiments, Compound 1 and/or tautomers thereof or a pharmaceutically acceptable salt or hydrate thereof is administered at a dose of from about 30 mg to about 120 mg per day, e.g., about 80 mg per day. In other embodiments, the dose may be from about 20 mg to about 100 mg per day or from about 20 mg to about 60 mg per day. For example, Compound 1 and/or tautomers thereof or a pharmaceutically acceptable salt or hydrate thereof may be administered in a 50 mg dose once per day, or in a 25 mg dose twice per day. In some embodiments, Compound 1 and/or tautomers thereof or a pharmaceutically acceptable salt or hydrate thereof is administered daily (e.g., once daily or twice daily) during a treatment period for at least 5 days, at least 7 days, at least 10 days, or at least 14 days (e.g., at about 50 mg per day). In some embodiments, after administration of Compound 1 and/or tautomers thereof or a pharmaceutically acceptable salt or hydrate thereof during a treatment period, a resting period commences and the patient is not administered the drug for at least 3, at least 5, at least 7, at least 10 or at least 14 days. For example, Compound 1 and/or tautomers thereof or a pharmaceutically acceptable salt or hydrate thereof may be administered daily for 14 days followed by a 7 day rest period during which the drug is not administered. Alternatively, Compound 1 and/or tautomers thereof or a pharmaceutically acceptable salt or hydrate thereof may be administered for 21 days followed by a 7 day rest period, or for 14 days followed by a 14 day rest period, or for 7 days followed by a 7 day rest period. In some embodiments, Compound 1 and/or tautomers thereof or a pharmaceutically acceptable salt or hydrate thereof may be administered on a 21 day cycle, or alternatively on a 14 day cycle or 28 day cycle. The dosages and dosing schedules may be used for treatment of cancer. In some embodiments, Compound 1 is administered to a patient in a fasted state.

Diagnostic Reagents

The present disclosure also provides a diagnostic reagent for predicting the likelihood that a patient will respond therapeutically to a cancer treatment comprising the administration of Compound 1 and/or tautomers thereof or a pharmaceutically acceptable salt or hydrate thereof, which comprises a reagent for detecting TP53 mutation status and/or hypermutation (e.g., MSI/MSS) status. The diagnostic reagent may be included in a kit as a component for determining the status(es), and the kit may further comprise instructions for using the diagnostic reagent for determining the status of mutation(s).

Examples of the reagent for detecting TP53 mutation status and/or hypermutation (e.g., MSI/MSS) status include (1) a nucleic acid probe capable of specifically detecting at least one mutation in a genome or mRNA sequence encoding the gene (preferably, ORF in a genome or mRNA sequence encoding the gene), or (2) a primer capable of specifically amplifying a region containing at least one mutation in a genome or mRNA sequence encoding the gene (preferably, ORF in a genome or mRNA sequence encoding the gene) and the like.

In some embodiments, determining of the TP53 mutation status and/or hypermutation status (e.g., MSS/MSI status) is accomplished using a next generation sequencing method. In some embodiments, determining of the TP53 mutation status and/or hypermutation status (e.g., MSS/MSI status) is accomplished using whole exome sequencing (WES) or RNA sequencing (RNASeq).

The diagnostic reagent of the present disclosure may be combined with various enzymes, enzyme substrates, buffers and the like according to the detection method of the present disclosure. Examples of the enzyme include enzymes necessary for various analysis methods exemplified as the detection method of the above-mentioned mutation, such as DNA polymerase, DNA ligase, restriction enzyme and the like. As the buffer, a buffer preferable for the maintenance of the activity of enzyme used for the analyses is appropriately selected. As the enzyme substrate, for example, a substrate for complementary chain synthesis and the like are used.

Using the diagnostic reagent of the present disclosure, the likelihood that a patient will respond therapeutically to a cancer treatment comprising the administration of Compound 1 and/or tautomers thereof or a pharmaceutically acceptable salt or hydrate thereof may be predicted according to the methods described herein.

The present disclosure also provides a kit for use in treating a patient with a cancer, comprising the above-mentioned diagnostic reagent of the present disclosure and a therapeutically effective amount of Compound 1 and/or tautomers thereof or a pharmaceutically acceptable salt or hydrate thereof. Compound 1 and/or tautomers thereof or a pharmaceutically acceptable salt or hydrate thereof may be provided as a medicament or a pharmaceutical composition comprising a therapeutically effective amount of Compound 1 and/or tautomers thereof or a pharmaceutically acceptable salt or hydrate thereof.

The kit of the present disclosure may further comprise instructions to administer Compound 1 and/or tautomers thereof or a pharmaceutically acceptable salt or hydrate thereof to the patient if the biomarker mutation status suggests that treatment is indicated.

Using the kit of the present disclosure, a patient with a cancer having an increased likelihood that the patient will respond therapeutically to a cancer treatment comprising the administration of Compound 1 and/or tautomers thereof or a pharmaceutically acceptable salt or hydrate thereof (i.e., a patient with a cancer who is predicted to be likely to respond therapeutically well to the cancer treatment with Compound 1 and/or tautomers thereof or a pharmaceutically acceptable salt or hydrate thereof) may be easily selected and treated by administering a therapeutically effective amount of Compound 1 and/or tautomers thereof or a pharmaceutically acceptable salt or hydrate thereof to cancer patients predicted, according to the above-mentioned prediction method of the present disclosure.

EXAMPLES

Example 1: Identification of Predictive Biomarker Signatures for Compound 1

Compound 1 is an investigational drug under clinical development for cancer treatment. Compound 1 achieves anti-tumor effects by inhibiting Cdc7 kinase, which is involved in DNA replication and repair. Predictive biomarker identification was investigated using data derived from a phase 2-like preclinical study, that is human primary tumor xenograft models using Balb/c nude mice (NOD/SCID, female, 6-8 weeks old, 18-22 g). For each model, 6 tumor bearing mice were randomized into 2 groups. Tumor fragments from seed mice inoculated with selected PDX tumors were harvested and used for inoculation into Balb/c nude mice. Each mouse was inoculated subcutaneously at the right flank with one tumor fragment (2-3 mm in diameter). The treatments were started when mean tumor size reached approximately 200-250 mm³. Mice were dosed orally with either vehicle or Compound 1 (crystalline form A of Compound 1 hemihydrate, 60 mg/kg, Bid, po, 21 days, 3 days on 4 days off). TP53 mutation status and hypermutation status as measured by microsatellite instability/stability (MSI/MSS) status were identified as predictive biomarkers for cancer treatment with Compound 1. FIG. 1 shows the % ΔTGI (total growth inhibition) by cancer type of the phase 2-like preclinical study.

Example 2: Predictive Biomarker Algorithm

An algorithm was developed to differentiate sensitive (responding) samples and resistant (non-responding) samples from the phase 2-like data.

2-1. Next Generation Sequencing Data Processing

Whole exome sequencing (WES) and RNA sequencing (RNASeq) were done for 92 xenograft models whose cancer types are colon (n=40), pancreas (n=24), non-small cell lung (n=23), and ovary cancer (n=5).

2-2. Data Quality Control (QC) for Whole Exome Sequencing (WES)

To raw mutation found by WES, filtering was applied in order to keep only high quality mutations. A total of 10,256,787 raw mutations were obtained first and mutations with read depths more than 20 and mutation allele frequency larger than 5% were retained. Only non-silent mutations such as non-synonymous point mutations, frame-shift/in-frame small insertions and deletions, stop gain and loss variants, splice variants were kept since mutations affecting protein translation are considered. However, even after the filtering, potential germline variants/SNPs still remain because no matched germline samples were available in this case. Therefore, mutations reported by widely used germline SNP databases (e.g. dbSNP, 1000 genome, ESP65000, and ExAC) were removed as these mutations are likely to be germline variants. Also, mutations with mutation allele frequency larger than 1% were kept. Next, in order to keep more functional mutations in disease, non-synonymous single nucleotide variants were tested by RadialSVM and SIFT and the ones predicted as significantly deleterious were retained. Finally, only driver mutations were kept by holding mutations.

2-3. Therapeutic Endpoints

In this study, % ΔTGI (percent delta tumor growth inhibition) was used and its mathematical definition is as follows.

$$\% \, \Delta TGI = 100 \times \left(1 - \frac{T_t - T_0}{C_t - C_0}\right)$$

In the above equation, $T_t$ and $T_0$ represent the sizes of tumor in treatment at time t and 0 and similarly $C_t$ and $C_0$ mean the sizes of tumor in control (vehicle) at the same time points t and 0. Therefore, a large % ΔTGI indicates a higher degree of tumor growth inhibition in treatment than in vehicle.

2-4. Algorithm Development and Biomarker Identification

Binary response was inferred by categorizing % ΔTGI, so that samples were classified as responders with high % ΔTGI and non-responders with low % ΔTGI. Chi-square test was run to evaluate the potential association between the class labels (responder vs. non-responder) and mutational status (MUT vs. WT). A total of 20 genes passed the p-value threshold of 0.05 and the 20 genes are as shown below: TP53, ACVR2A, LRP1B, CTNNB1, SEC31A, ABCB4, HERC2, DNM2, FXR1, BAX, ATR, APC, CHD8, CTCF, CHD2, PIK3CA, CLOCK, CNOT1, STAT5B, CHD3.

Figure 2:
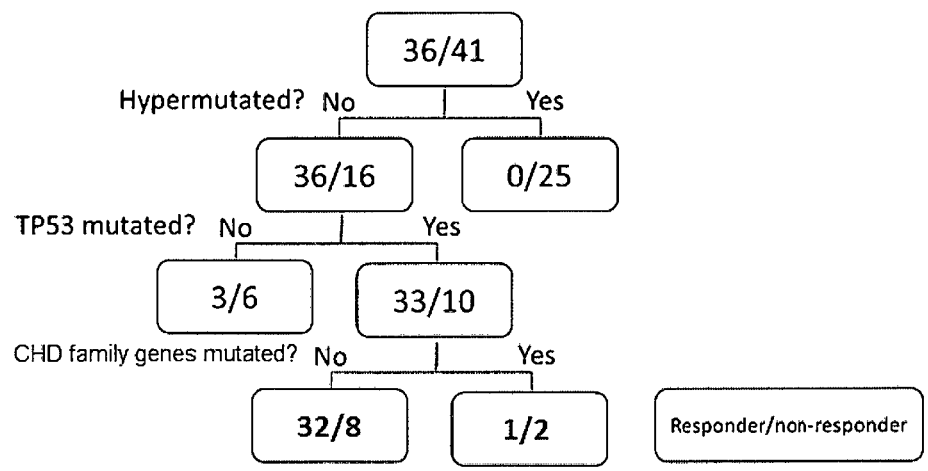
FIG. 2 is a tree chart showing the number of responding and non-responding samples for hypermutation status, TP53 mutation status and CHD family genes mutation status.

A decision tree summary of a total of 77 models with response and non-responder status using above-mentioned 20 genes etc. is shown in FIG. 2. Among 92 models which used in above-mentioned 2-1, intermediate response models (15 models) were excluded from the analysis. This association revealed that TP53 mutation was most significantly associated with response. This association also revealed models with hypermutation were associated with non-response. This association revealed that CHD family genes mutation was associated with non-response.

2-5. Predict Cancer Indications Likely to be Responsive to Compound 1

Cancer types likely to respond to Compound 1 treatment using the algorithm explained above were investigated. The Cancer Genome Atlas (TCGA) mutation data was downloaded for the 20 mutations and CHD family genes, and the algorithm was run on each cancer type to predict responders to Compound 1 (FIG. 3).

Figure 3:
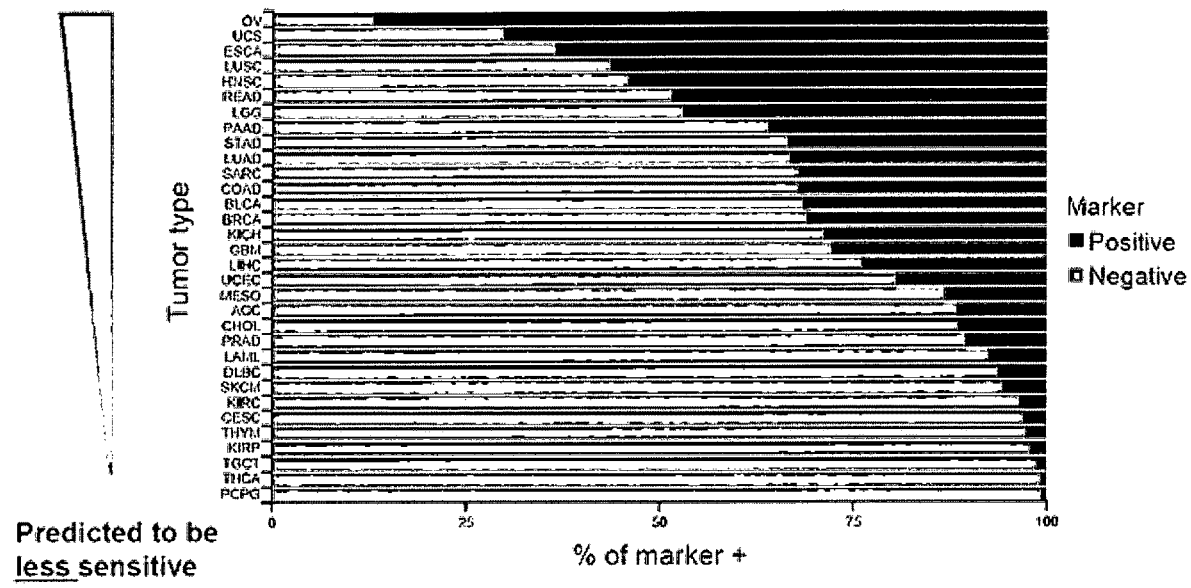
FIG. 3 is a TCGA genetic/genomic data were scanned by the algorithm in order to identify cancer indications enriched with the biomarker signatures.

Meaning of abbreviations in FIG. 3 is as follows.

| Tumor type code | Full name |
| --- | --- |
| OV | Ovarian serous cystadenocarcinoma |
| UCS | Uterine Carcinosarcoma |
| ESCA | Esophageal carcinoma |
| LUSC | Lung squamous cell carcinoma |
| HNSC | Head and Neck squamous cell carcinoma |
| READ | Rectum adenocarcinoma |
| LGG | Brain Lower Grade Glioma |
| PAAD | Pancreatic adenocarcinoma |
| STAD | Stomach adenocarcinoma |
| LUAD | Lung adenocarcinoma |
| SARC | Sarcoma |
| COAD | Colon adenocarcinoma |
| BLCA | Bladder Urothelial Carcinoma |
| BRCA | Breast invasive carcinoma |
| KICH | Kidney Chromophobe |
| GBM | Glioblastoma multiforme |
| LIHC | Liver hepatocellular carcinoma |
| UCEC | Uterine Corpus Endometrial Carcinoma |
| MESO | Mesothelioma |
| ACC | Adrenocortical carcinoma |
| CHOL | Cholangiocarcinoma |
| PRAD | Prostate adenocarcinoma |
| LAML | Acute Myeloid Leukemia |
| DLBC | Lymphoid Neoplasm Diffuse Large B-cell Lymphoma |
| SKCM | Skin Cutaneous Melanoma |
| KIRC | Kidney renal clear cell carcinoma |
| CESC | Cervical squamous cell carcinoma and endocervical adenocarcinoma |
| THYM | Thymoma |
| KIRP | Kidney renal papillary cell carcinoma |
| TGCT | Testicular Germ Cell Tumors |
| THCA | Thyroid carcinoma |
| PCPG | Pheochromocytoma and Paraganglioma |
| UVM | Uveal Melanoma |

Based on this observation and biological and clinical knowledge on Compound 1, ovarian serous cystadenocarcinoma, esophageal carcinoma (e.g., squamous esophageal cancer), lung squamous cell carcinoma (e.g., squamous non-small cell lung cancer), head and neck squamous cell carcinoma, rectum/colon adenocarcinoma and pancreatic adenocarcinoma etc. were identified as cancer types which are likely to be highly responsive to Compound 1.

Example 3: An Open-Label, Phase 2, Parallel Arm Study to Evaluate the Safety, Tolerability, and Activity of Compound 1 Single Agent in Patients with Squamous NSCLC or Squamous Esophageal Cancer Compound 1 is investigated in a phase 2, multicenter, single agent, uncontrolled, open-label parallel arm trial in squamous NSCLC or squamous esophageal cancer. The form of Compound 1 used in the study is Crystalline Form I Compound 1 hemihydrate. The safety, tolerability, and pharmacokinetics (PK) of Compound 1 are evaluated for administration of 50 mg QD (once daily) of Compound 1 for 14 days in a 21-day cycle. Treatment duration continues until a discontinuation criterion is met or 1 year of dosing. Patients with clinical benefit may continue after 1 year.

The primary endpoints for this study are (1) frequency of treatment-emergent adverse events (TEAEs): dose-limiting toxicities, serious adverse events, TEAEs leading to dose modifications, and TEAEs leading to treatment discontinuation; (2) disease control rate (DCR) per RECIST v. 1.1 in the disease specific cohorts: complete response (CR)+partial response (PR)+stable disease (SD) (SD has to be at least 6 weeks from treatment initiation to qualify for DCR).

Secondary endpoints are (1) PK parameters after the first dose of Compound 1 on Cycle 1, Day 1: $C_{max}$, $t_{max}$, $AUC_{24}$, AUC from time 0 to the time of the last quantifiable concentration ($AUC_{last}$) and renal clearance; (2) PK parameters after multiple doses of Compound 1: $C_{max}$, $t_{max}$, $AUC_{24}$, $AUC_{last}$, terminal disposition phase half-life, steady-state apparent oral clearance, and accumulation ratio based on AUC over the dosing interval; (3) overall response rate (ORR) (CR+PR), (4) duration of response (DOR), (5) progression-free survival (PFS), (6) overall survival (OS); and (7) percentage of patients with TEAEs.

The study will evaluate the antitumor activity of Compound 1 as a single agent in patients with locally advanced or metastatic squamous esophageal cancer and patients with locally advanced or metastatic squamous non-small cell lung cancer (NSCLC). The study will evaluate the dose and dosing schedule of 50 mg QD for 14 days in 21 day cycles.

In human hepatocytes, Compound 1 can be metabolized to compounds of the following structures:

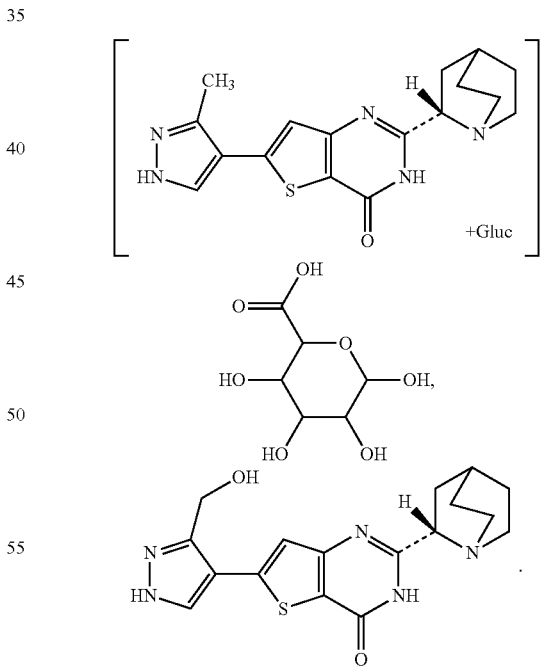

Compound 1 is administered orally to patients on an empty stomach and should be taken with at least 8 ounces of water. The standard dose of 50 mg QD can be reduced to 40 mg and reduced further to 30 mg as appropriate. TP53 mutation status and/or hypermutation (e.g., MSI/MSS) status may be used as inclusion/exclusion criteria for the study.

We claim:

1. A method of determining whether to treat a patient having cancer with Compound 1 and/or tautomers thereof or a pharmaceutically acceptable salt or hydrate thereof comprising:

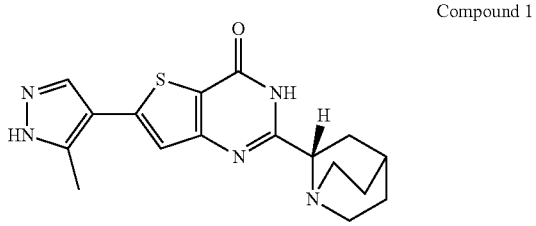 [SMILES: Cc1[nH]ncc1-c1cc2nc([C@@H]3CC4CCN3CC4)[nH]c(=O)c2s1]

Compound 1 determining a TP53 mutation status and a hypermutation status from one or more samples from the patient, and determining to treat the patient with a therapeutically effective amount of Compound 1 and/or tautomers thereof or a pharmaceutically acceptable salt or hydrate thereof if the one or more samples (i) have the presence of TP53 mutation(s) and (ii) test negative for hypermutation.

2. The method of claim 1, wherein the sample tests negative for hypermutation if the sample has microsatellite stability (MSS) status.

3. The method of claim 1, wherein the cancer is selected from squamous esophageal cancer and squamous non-small cell lung cancer.

4. The method of claim 1, wherein Compound 1 and/or tautomers thereof or a pharmaceutically acceptable salt or hydrate thereof is provided as a hemihydrate of Compound 1.

5. The method of claim 4, wherein the hemihydrate of Compound 1 is provided as Crystalline Form 1 of the hemihydrate of Compound 1.

6. A method of treating cancer comprising:

determining a TP53 mutation status and a hypermutation status of one or more samples from a patient, and administering a therapeutically effective amount of Compound 1 and/or tautomers thereof or a pharmaceutically acceptable salt or hydrate thereof

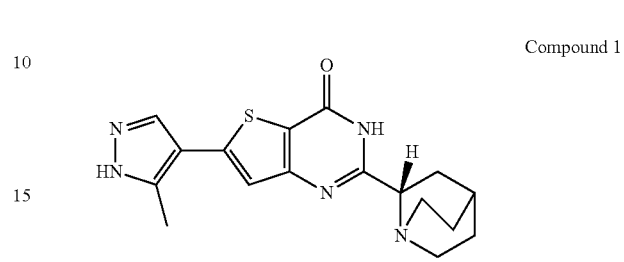

Compound 1 to the patient if the one or more samples (i) have the presence of TP53 mutation(s) and (ii) test negative for hypermutation.

7. The method of claim 6, wherein the sample tests negative for hypermutation if the sample has microsatellite stability (MSS) status.

8. The method of 6, wherein the cancer is selected from squamous esophageal cancer and squamous non-small cell lung cancer.

9. The method of claim 6, wherein the Compound 1 and/or tautomers thereof or a pharmaceutically acceptable salt or hydrate thereof is provided as a hemihydrate of Compound 1.

10. The method of claim 9, wherein the hemihydrate of Compound 1 is provided as Crystalline Form I of the hemihydrate of Compound 1.

* * * * *